United States Patent
Lin

(10) Patent No.: US 10,149,868 B2
(45) Date of Patent: Dec. 11, 2018

(54) **USE OF *STREPTOCOCCUS THERMOPHILIS* TCI633 IN TREATING ARTHRITIS**

(71) Applicant: TCI CO., LTD., Taipei (TW)

(72) Inventor: Yung-Hsiang Lin, Taipei (TW)

(73) Assignee: TCO CO., LTD., Taipei (TW)

( * ) Notice: Subject to any disclaimer, the term of this patent is extended or adjusted under 35 U.S.C. 154(b) by 0 days.

(21) Appl. No.: 15/608,810

(22) Filed: May 30, 2017

(65) Prior Publication Data
US 2017/0340681 A1  Nov. 30, 2017

Related U.S. Application Data

(60) Provisional application No. 62/343,475, filed on May 31, 2016.

(30) Foreign Application Priority Data

Feb. 2, 2017  (TW) .............................. 106103487 A

(51) Int. Cl.
*A61K 39/02* (2006.01)
*A61K 35/74* (2015.01)
*A61K 35/744* (2015.01)

(52) U.S. Cl.
CPC ............ *A61K 35/74* (2013.01); *A61K 35/744* (2013.01)

(58) Field of Classification Search
None
See application file for complete search history.

(56) References Cited

FOREIGN PATENT DOCUMENTS

| JP | 2012023996 | * | 2/2012 |
| JP | 2012050889 | * | 8/2012 |
| KR | 2012002543 | * | 3/2012 |

* cited by examiner

*Primary Examiner* — Jennifer E Graser
(74) *Attorney, Agent, or Firm* — Christensen, Fonder, Dardi & Herbert PLLC

(57) ABSTRACT

A method of treating arthritis, which comprising administering to a subject in need an effective amount of *Streptococcus thermophilus* DSM 28121 strain. The method is especially used for relieving joint pain, alleviating joint swelling, relieving tissue inflammation, protecting cartilaginous tissues and increasing the number of chondrocytes in the cartilaginous tissues.

20 Claims, 9 Drawing Sheets

USE OF *STREPTOCOCCUS THERMOPHILUS* TCI633 IN TREATING ARTHRITIS

FIELD OF THE INVENTION

The present invention relates to the use of *Streptococcus thermophilus* TCI633. The present invention especially relates to the use of *Streptococcus thermophilus* TCI633 in treating arthritis, which includes relieving joint pain, alleviating joint swelling, relieving tissue inflammation, protecting cartilaginous tissue and increasing the number of chondrocytes in the cartilaginous tissues, wherein TCI633 was deposited at German Collection of Microorganisms and Cell Cultures (Deutsche Sammlung von Mikroorganismen und Zellkulturen GmbH, DSMZ) under the accession number DSM 28121.

BACKGROUND OF THE INVENTION

In clinic, arthritis can be roughly classified as osteoarthritis, rheumatoid arthritis, gouty arthritis and bacterial arthritis. These types are different from each other in the symptoms and predilection site. Osteoarthritis, which belongs to degenerative joint diseases, is the most common type of arthritis. For patients with osteoarthritis, the attack on the articular cartilage would result in not only pain but also rigidity, swelling, deformity and other symptoms. The persistence of those symptoms may cause difficulties in movement, and thus, the assistance from crutches or wheelchairs is needed.

In general, osteoarthritis primarily occurs in the joints that need to move frequently and bear weight, such as knee joints, hip joints, metacarpophalangeal joints, lumbar spines and cervical spines. The main therapeutic method for treating osteoarthritis is non-surgical therapy including drug therapy, rehabilitation therapy and hyaluronic acid injection. Surgical therapy will be performed only if the above non-surgical therapies cannot relieve the symptoms of patients.

In the aspect of drug therapy, though steroids can be used to relieve patient's pain, the use of steroids is often accompanied by osteoporosis, poor wound healing, skin thinning, upper gastrointestinal bleeding, and other side effects, and will even increase blood pressure and exacerbate diabetes. Therefore, currently, most patients with arthritis do not use steroids anymore, however, some patients with rheumatoid arthritis, lupus erythematosus, ankylosing spondylitis, and spinal trauma still need to use steroids for relieving pain. Drugs that can be used to replace steroids include nonsteroidal anti-inflammatory drugs and glucosamine. At present, non-steroidal anti-inflammatory drugs are widely used because of their analgesic effect. However, long-term use of nonsteroidal anti-inflammatory drugs will cause peptic ulcer, edema of the lower limbs, impairment of kidney function and other side effects, and thus, one should be careful while using the nonsteroidal anti-inflammatory drugs. As for glucosamine, it is capable of stimulating the chondrocytes in the joints to synthesize glycoproteins and simultaneously providing anti-inflammatory and analgesic effects. In addition, glucosamine does not cause the same side effects of non-steroidal anti-inflammatory drugs. Thus, glucosamine has been used in the treatment of many arthritis patients. However, the clinical outcome showed that there is a considerable diversity among patients in the capacity of absorbing glucosamine, and thus, the dose of glucosamine cannot be efficiently controlled and adjusted. Furthermore, the clinical outcome also showed that glucosamine is ineffective in many patients.

When the above non-surgical therapies cannot alleviate the symptoms and mitigate the pain of patients, an invasive surgical therapy (such as arthroscopic surgery) would be the only approach for removing foreign matter in the joint cavity or repairing the damaged cartilage. However, surgery has only a very limited effect on patients with severely damaged joints. At present, it is also common to adopt artificial joint replacement as a treatment. However, the artificial joint has a limited life span, and the cost of using pure metal or ceramic artificial joints with longer life span is quite high.

Therefore, it will be of a great help to find a therapeutic method capable of providing a long-lasting effect on the patients with arthritis, especially in relieving the patient's pain, at a manner that is cost-effective, non-invasive and with minimal side effects.

SUMMARY OF THE INVENTION

An objective of the present invention is to provide a method of treating arthritis, comprising administering to a subject in need an effective amount of *Streptococcus thermophilus* TCI633 strain which was deposited at German Collection of Microorganisms and Cell Cultures (DSMZ) under the accession number DSM 28121, wherein the method is for at least one of relieving joint pain, alleviating joint swelling, relieving tissue inflammation, protecting cartilaginous tissue or increasing the number of chondrocytes in the cartilaginous tissues.

The detailed technology and some particular embodiments implemented for the present invention are described in the following paragraphs for people skilled in this field to well appreciate the features of the claimed inventive.

DESCRIPTION OF THE PREFERRED EMBODIMENTS

Figure 1:
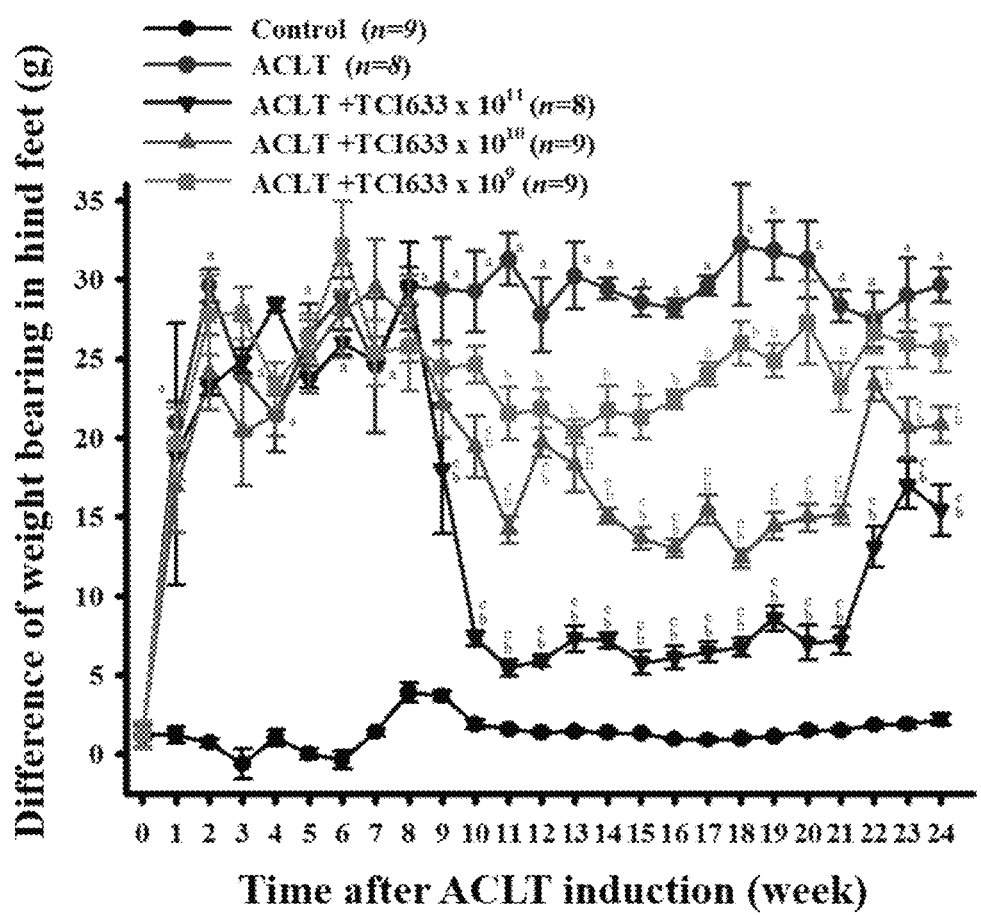
FIG. 1 is a comparative result diagram, showing the effects of different TCI633 doses on the ACLT-induced changes of hind paw weight bearing distribution as illustrated in the examples.

The detailed technology and preferred embodiments implemented for the present invention are described in the following paragraphs for people skilled in the field to well appreciate the features of the claimed invention. However, without departing from the spirit of the present invention, the present invention may be realized in various embodiments and the present invention and should not be limited to the embodiments described in the specification.

In addition, unless otherwise stated herein, the expressions "a," "an," "the," or the like recited in this specification (especially in the claims) should be interpreted to include both the singular and plural forms. Furthermore, the term "an effective amount" used in this specification refers to the dose that can at least partially alleviate or persistently reduce the symptoms and/or signs of arthritis (such as pain and joint rigidity) in a suspected subject while being administered to the subject. The unit "CFU/kg-body weight" used in this specification refers the dosage required per kg of body weight.

In addition, unless otherwise stated herein, the term "subject" used in this specification of the present invention (especially in the claims) refers to a mammalian, including human and non-human animals. The terms "treat" and "treating" used in this specification refers to reducing or delaying one or more influences/symptoms of arthritis, including reducing the basic causes of arthritis.

Inventors of the present invention found that TCI633 strain can provide the following effects to a subject with arthritis, while without causing side effects: relieving joint pain, alleviating joint swelling, relieving tissue inflammation, protecting cartilaginous tissue and increasing the number of chondrocytes in the cartilaginous tissues. Therefore, the TCI633 strain is safe for long term use for reducing the torment caused by pain, swelling and inflammation, as well as reducing the movement difficulties and inconveniences and improving the quality of the patient's life. Therefore, the present invention is directed to the use of the *Streptococcus thermophilus* TCI633 strain in treating arthritis, comprising administering to a subject in need the TCI633 strain.

The TCI633 strain adopted by the present invention could be provided in a form of dried bacterial powder for oral administration, and could be a form of being comprised in a pharmaceutical composition or medicament. The pharmaceutical composition or medicament used according to the present invention could be administered to a subject in need to treat arthritis by an oral route, a parenteral (e.g., intra-articular) route or combinations thereof. Depending on the form and purpose, suitable carriers could be chosen and used to provide the pharmaceutical composition or medicament, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the pharmaceutical composition or medicament provided by the present invention could comprise any pharmaceutically acceptable carrier that will not adversely affect the desired effects of TCI633 strain. For example, the pharmaceutically acceptable carrier could be water, saline, dextrose, glycerol, ethanol or its analogs, cellulose, starch, sugar bentonite, or combinations thereof. The pharmaceutical composition or medicament could be provided in any suitable form for oral administration, such as in the form of a powder, a tablet (e.g., dragee, chewable tablet), a pill, a capsule, a granule, a pulvis, a fluidextract, a solution, syrup, a suspension, a tincture, etc.

As for the form of injections or drips suitable for intra-articular injection, the pharmaceutical composition or medicament provided according to the present invention could comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the pharmaceutical composition or medicament as a powder for injection, a suspension for injection, or a powder suspension for injection, etc. Alternatively, the pharmaceutical composition or medicament could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the pharmaceutical composition or medicament provided according to the present invention could further comprise a suitable amount of additives, such as a flavoring agent, a toner, or a coloring agent for enhancing the palatability and the visual perception of the pharmaceutical composition or medicament, and/or a buffer, a conservative, a preservative, an antibacterial agent, or an antifungal agent for improving the stability and storability of the pharmaceutical composition or medicament. In addition, the pharmaceutical composition or medicament could optionally further comprise one or more other active ingredient(s) (such as hyaluronic acid), or be used in combination with a medicament comprising one or more other active ingredient(s), to further enhance the effects of the pharmaceutical composition or medicament, or to increase the application flexibility and adaptability of the preparation thus provided, as long as the other active ingredients will not adversely affect the desired effects of the TCI633 strain.

Depending on the need, age, body weight, and health conditions of the subject, the dried bacterial powder, pharmaceutical composition and medicament for oral administration adopted according to the present invention could be dosed with various administration frequencies, such as once a day, multiple times a day, or once every few days, etc. For example, when the dried bacterial powder, pharmaceutical composition or medicament is applied orally to a subject for treating arthritis, the dried bacterial powder, pharmaceutical composition or medicament is administrated at a daily amount of at least $8.06 \times 10^8$ CFU (as TCI633 strain)/kg-body weight, preferably ranging from $8.06 \times 10^8$ CFU (as TCI633 strain)/kg-body weight to $8.06 \times 10^{10}$ CFU (as TCI633 strain)/kg-body weight, and more preferably ranging from $8.06 \times 10^9$ CFU (as TCI633 strain)/kg-body weight to $8.06 \times 10^{10}$ CFU (as TCI633 strain)/kg-body weight.

The present invention will be further illustrated in detail with specific examples as follows. However, the following examples are provided only for illustrating the present invention and the scope of the present invention is not limited thereby. The scope of the present invention will be indicated in the appended claims.

Cultivation of TCI633 Strain

*Streptococcus thermophilus* TCI633 strain (deposited at German Collection of Microorganisms and Cell Cultures (DSMZ) under the accession number DSM 28121) adopted by the present invention was isolated from healthy people's breast milk. TCI633 strain stored in glycerol could be inoculated onto MRS medium (1%, v/v) for 16 to 24 hours, and then transferred into a medium containing 20 g/L to 60 g/L glucose, 5 g/L to 30 g/L sucrose, 10 g/L to 20 g/L yeast extract, 5 g/L to 10 g/L peptone, 2.5 g/L to 8 g/L $K_2HPO_4$, 1 g/L to 2 g/L sodium chloride and 0.5 g/L to 1.2 g/L $MgSO_4 \cdot 7H_2O$, to being cultured at 37° C. for 48 hours.

Establishment of the Animal Model

In the example of the present invention, experimental male rats (Wistar rat, 8 weeks of age) were purchased from BioLASCO Co., Ltd. (Taipei, Taiwan), and were housed for about 10 days in an environmentally controlled animal facility at 24±1° C. and 50-55% relative humidity under a day/night cycle of 12/12 hours at the Marine Biomedical Pre-clinical Test Core Laboratory, Department of Marine Biotechnology and Resources, Sun Yat-sen University. The rats weighed about 300±10 grams (at 9-10 weeks of age) when the experiment started. All surgeries and infusion procedures for the model were performed under anesthesia with 2.5% isoflurane (Catalog No. 08547, Panion & BF Biotech Inc., Taoyuan, Taiwan). All the operations and uses of animal tests were performed in accordance with the Guiding Principles in the Care and Use of Animals of the American Physiology Society and with the permission of the Institutional Animal Care and Use Committee of National Sun Yat-sen University.

In animal model, a rat model with ACLT-induced (anterior cruciate ligament transected) osteoarthritis was established according to the procedures provided in the papers published by Stoop et al. in 2001 and Yang et al. in 2014. First, baseline measurements of animal behaviors were performed, and then the rats were anesthetized and had their both knees areas shaved. Then, the skin of the knees was disinfected with alcohol and a medial parapatellar incision was made. After the knee joint capsule was opened, the patella was dislocated laterally to place the right knee in full flexion to reveal the anterior cruciate ligament. The middle part of the right anterior cruciate ligament was transected using a sharp knife and an anterior draw test was performed to ensure the complete transection of the ligament. After, surgical suturing was performed. The procedures for the control group consisted only of opening the joint capsule of the knee, without performing the anterior cruciate ligament transection (Stoop, et al., 2001). After the surgery, cefazolin (20 mg/kg) was administered to prevent wound infection. The rats were then returned to their cages to allow freedom of movement for 8 weeks. Animal behavior tests were performed weekly to ascertain whether the pain and swelling behavior of the ACLT groups were significantly different from those rats of normal group (control group), and TCI633 probiotics were administered after that.

Experimental rats were divided into five groups:

a. Control group: normal rats were subjected to a procedure of opening joint capsule of the knee without inducing arthritis (i.e., the anterior cruciate ligament was not transected), and were orally administered with excipient (provided by First Tek, Inc., Taiwan) every day from 8 to 20 weeks after surgery.

b. ACLT group: the excipient was orally administered every day from 8 to 20 weeks after the surgical induction of arthritis.

c. "ACLT+TCI633 ($5 \times 10^{11}$ CFU)" group: the TCI633 powder (provided by First Tek, Inc., Taiwan) was orally administered at a daily amount of $5 \times 10^{11}$ CFU/kg-body weight from 8 to 20 weeks after the surgical induction of arthritis.

d. "ACLT+TCI633 ($5 \times 10^{10}$ CFU)" group: the TCI633 powder was orally administered at a daily amount of $5 \times 10^{10}$ CFU/kg-body weight from 8 to 20 weeks after the surgical induction of arthritis.

e. "ACLT+(TCI633 $5 \times 10^9$ CFU)" group: the TCI633 powder was orally administered at a daily amount of $5 \times 10^9$ CFU/kg-body weight from 8 to 20 weeks after the surgical induction of arthritis.

Data Analysis

The experimental data for all of the following examples are expressed as mean±SEM. A t-test was used to compare the data of two groups. For comparing multiple groups, one-way analysis of variance (ANOVA) was used to analyze the differences among groups, while Duncan's Method was used to compare the differences between subsets of groups. A P-value <0.05 was considered to represent a significant difference.

EXAMPLE 1

Test for Changes of Hind Paw Weight Bearing Distribution

Changes in weight bearing distribution between the paw with degenerative joint resulting from the ACLT and the paw in contralateral control group hind were utilized as an index of joint pain of osteoarthritis (Bove et al, 2006). Dual Channel Weight Averager (Singa Technology Corporation, Taiwan) was used to measure the weight borne by the left and right hind paws. First, rats were placed in a sloped channel so that each hind paw was standing on a separate scale which measured the weight borne by the left and right paws. After the rats were in a stable position and calm, the measurement button was pressed to record data after three seconds. The results were calculated by subtracting the paw with degenerative joint (right paw) from normal paw (left paw) (Fernihough, et al., 2004). This test was performed weekly from weeks 1 to 24 after the baseline measurements of animal behavior and the ACLT surgery, and the results are shown in FIG. 1.

As shown in FIG. 1, in the aspect of the change of hind paw weight bearing distribution induced by ACLT, the ACLT group showed a significant increase in the change of hind paw weight bearing distribution from weeks 1 to 24 compared with the control group. After the induction of arthritis, the ACLT+TCI633 ($5 \times 10^{11}$ CFU) showed a significant reduction in the change of hind paw weight bearing distribution from weeks 9 to 24 compared with the ACLT group. The ACLT+TCI633 ($5 \times 10^{10}$ CFU) group showed a significant reduction in the change of hind paw weight bearing distribution from weeks 10 to 24 compared with the ACLT group. The ACLT+TCI633 ($5 \times 10^9$ CFU) group showed a significant reduction in the change of hind paw weight bearing distribution from weeks 13 to 19 and 22 compared with the ACLT group. Wherein, at weeks 9 to 24, the ACLT+TCI1633 ($5 \times 10^{10}$ CFU) group and ACLT+TCI633 ($5 \times 10^{11}$ CFU) showed a significant reduction in the change of hind paw weight bearing distribution compared with ACLT+TCI633 ($5 \times 10^9$ CFU) group. The above results indicate that probiotic TCI633 provided a significant effect on reducing ACLT-induced change of hind paw weight bearing distribution, wherein the reduction was dose-dependent. As shown in Table 1, the percentage of analgesic effect (%) on the change of hind paw weight bearing distribution in each of the ACLT+TCI633 groups tended to decrease after administration was stopped.

TABLE 1

| Groups | Week | | | | |
|---|---|---|---|---|---|
| | week 20 | week 21 | week 22 | week 23 | week 24 |
| ACLT | 0 ± 7.8 | 0 ± 2.65 | 0 ± 5.36 | 0 ± 8.023 | 0 ± 3.68 |
| ACLT + TCI633(5 × $10^9$) | 12.72 ± 8.4 | 18.09 ± 5.34 | 2.64 ± 5.41 | 5.75 ± 5.20 | 9.95 ± 5.44 |
| ACLT + TCI633(5 × $10^{10}$) | 52.16 ± 2.88 | 44.02 ± 2.20 | 11.35 ± 4.07 | 15.79 ± 2.18 | 25.38 ± 3.69 |
| ACLT + TCI633(5 × $10^{11}$) | 77.44 ± 3.48 | 72.68 ± 2.51 | 49.49 ± 4.63 | 41.29 ± 5.30 | 44.21 ± 4.95 |
| Control group | | | | | |

EXAMPLE 2

Thermal Hyperalgesia Test

A thermal hyperalgesia test was performed according to the method disclosed in the paper published by Hargreaves et al. in 1988 by irradiating the animal's paw with a low-energy radiant heat light source to measure the withdrawal latencies. The thermal hyperalgesia behavior was analyzed by a plantar test. A Plantar Stimulator Analgesia Meter (Life science, SERIES 8 IITC Model 390, USA) was used and adjusted to an active intensity of 25. To avoid rats' paw tissue from suffering from long-term heat damage, the cut-off time for the irradiation was set to 30 seconds (Hargreaves et al., 1988). To assess nociceptive responses to thermal stimuli, rats were placed on an acrylic glass platform, and the middle area of the paws of the rats was exposed to a thermal source stimuli. Observation was made to record how long it took the rats to lift their paws off the platform. This test was performed weekly from weeks 1 to 24 after the baseline measurements of animal behavior and the ACLT surgery, and the results are shown in FIG. 2.

Figure 2:
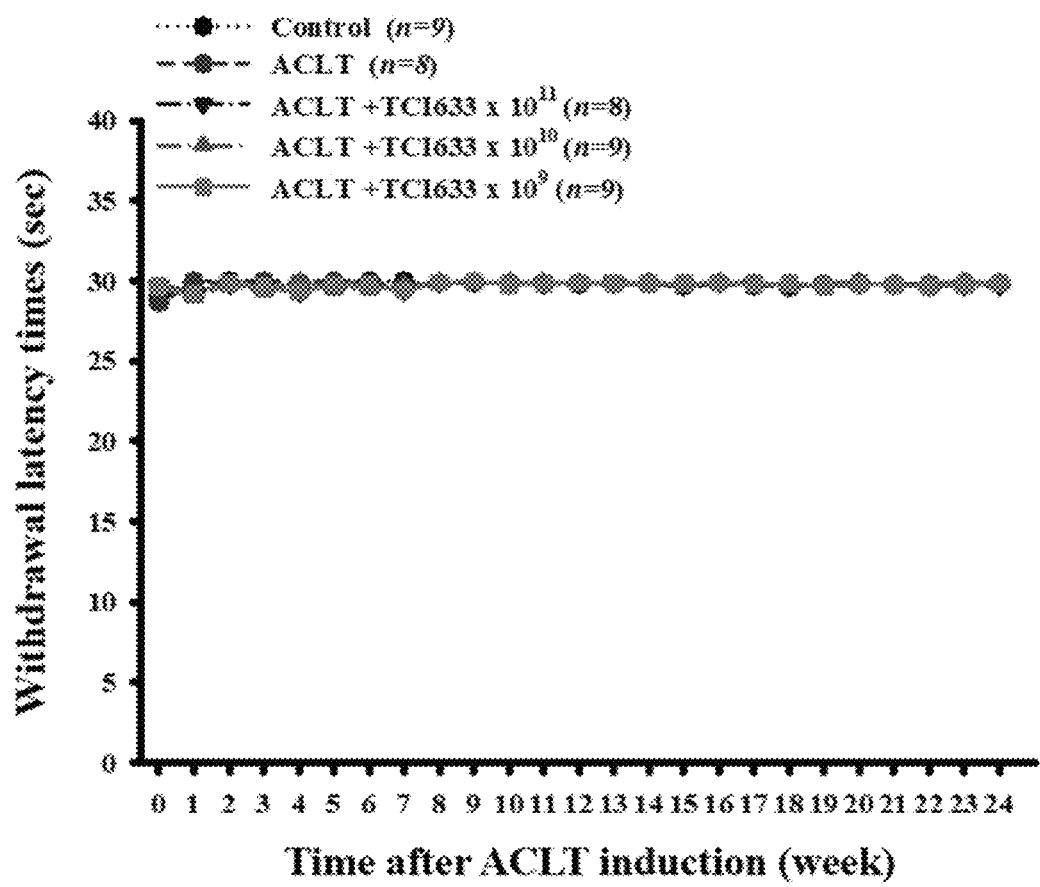
FIG. 2 is a comparative result diagram, showing the effects of different TCI633 doses on the thermal hyperalgesia as illustrated in the examples.

As shown in FIG. 2, ACLT group showed no significant difference in the change of thermal hyperalgesia from week 0 to 24 compared with the control group. After the induction of arthritis, each of the ACLT+TCI633 groups and ACLT group also showed no significant difference in the change of thermal hyperalgesia. The above results indicate that after the induction of osteoarthritis by surgery. TCI633 did not significantly change the thermal hyperalgesia, and the values of ACLT+TCI633 groups were similar to those in the control group. No significant effect was observed after administration was stopped.

Wood Dale, Ill., USA) from the bottom to the top to the hind paws of the rats. The intensity of the pressure was gradually increased from 1 g until the paw withdrawal behavior appeared, and then the pressure value was recorded as the withdrawal threshold. The pressure applied lasted for no more than 5 seconds each time, and the measurement was repeated for 3 times to ensure the accuracy of the data. Stimuli were presented at 15-second intervals or longer (Chaplan et al., 1994), and the results are shown in FIG. 3.

Figure 3:
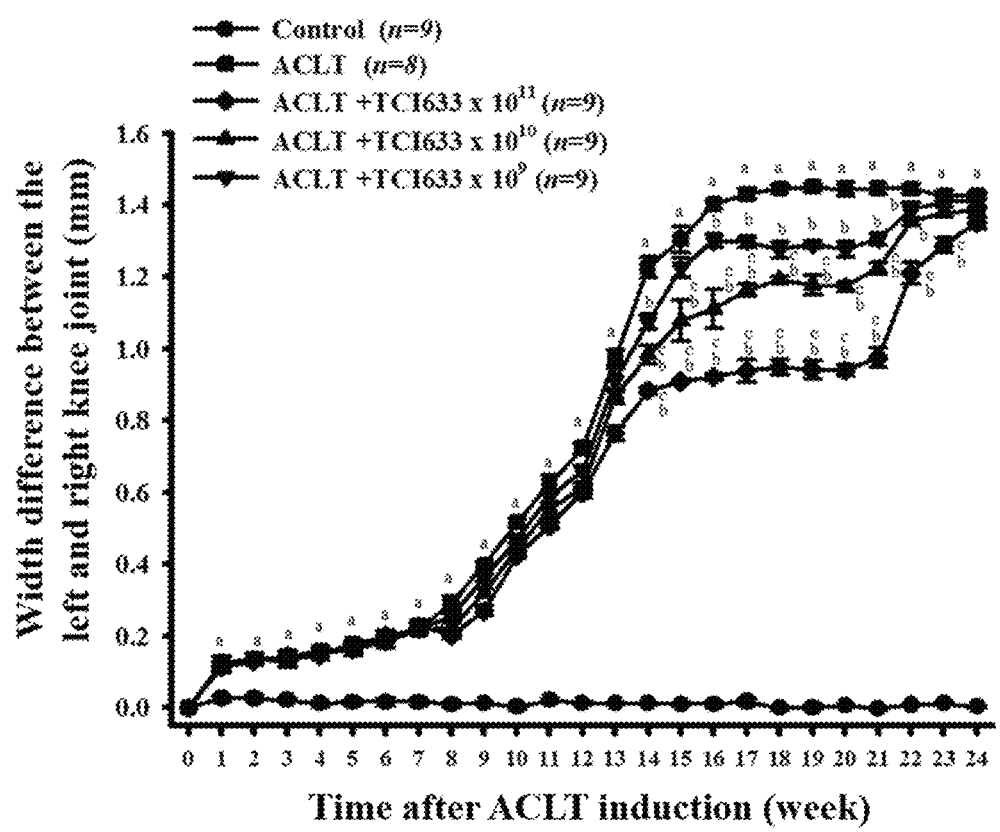
FIG. 3 is a comparative result diagram, showing the effects of different TCI633 doses on the ACLT-induced mechanical allodynia as illustrated in the examples.

As shown in FIG. 3, ACLT group showed a significant reduction in the threshold of the withdrawal response from weeks 6 to 24 compared with the control group. After the induction of arthritis, the ACLT+TCI633 ($5 \times 10^{11}$ CFU) group showed a significant increase in the threshold of the withdrawal response from weeks 9 to 24 compared with the ACLT group. The ACLT+TCI633 ($5 \times 10^{10}$ CFU) group showed a significant increase in the threshold of the withdrawal response from weeks 9 to 23 compared with the ACLT group. The ACLT+TCI633 ($5 \times 10^9$ CFU) group showed a significant increase in the threshold of the withdrawal response from weeks 13 to 22 compared with the ACLT group. Wherein, at weeks 9 to 22, the ACLT+TCI633 ($5 \times 10^{10}$ CFU) group and ACLT+TCI1633 ($5 \times 10^{11}$ CFU) group showed a significant increment in the threshold of the withdrawal response compared with ACLT+TCI633 ($5 \times 10^9$ CFU) group. The above results indicate that TCI633 strain provided a significant effect on reducing ACLT-induced mechanical allodynia, wherein the reduction was dose-dependent. As shown in Table 2, the percentage of analgesic effect (%) on the mechanical allodynia in each of the ACLT+TCI633 groups tended to decrease after administration was stopped.

TABLE 2

| Groups | Week | | | | |
|---|---|---|---|---|---|
| | week 20 | week 21 | week 22 | week 23 | week 24 |
| ACLT | 0 ± 0.89 | 0 ± 1.19 | 0 ± 1.17 | 0 ± 1.75 | 0 ± 0.8 |
| ACLT + TCI633(5 × $10^9$) | 15.60 ± 3.33 | 17.22 ± 3.96 | 7.65 ± 3.28 | 1.62 ± 2.22 | 0.07 ± 0.6 |
| ACLT + TCI633(5 × $10^{10}$) | 41.86 ± 3.39 | 38.89 ± 3.95 | 27.90 ± 4.66 | 11.02 ± 3.99 | 1.36 ± 1.33 |
| ACLT + TCI633(5 × $10^{11}$) | 64.17 ± 3.71 | 63.26 ± 3.43 | 50.01 ± 4.01 | 33.78 ± 3.99 | 14.87 ± 4.37 |
| Control group | | | | | |

EXAMPLE 3

Mechanical Allodynia Test

The effects of TCI633 on ACLT-induced mechanical allodynia were evaluated according to the method disclosed in the paper published by Chaplan et al. in 1994. The rats were placed in a brown acrylic box with a wire mesh bottom and allowed to acclimate for 15 minutes. Then, perpendicular pressure was applied by Von Frey filaments (Stoelting,

EXAMPLE 4

Measurement of the Width of Knee Joint Swelling

Width changes of the knee joints were measured weekly before the ACLT (baseline) and from 1 to 24 weeks after the surgery to evaluate knee inflammation. After the rats were anesthetized with 2.5% isofurane, the widths of the left and right knee joints of each rat were measured with calipers (AA847R, Aesculap, AG& CO, KG German), and the measurements were recorded carefully (Yang et al., 2014). Results were calculated by subtracting the width of the normal paw (left paw) from the paw with degenerative joint (right paw), and the results are shown in FIG. 4.

Figure 4:
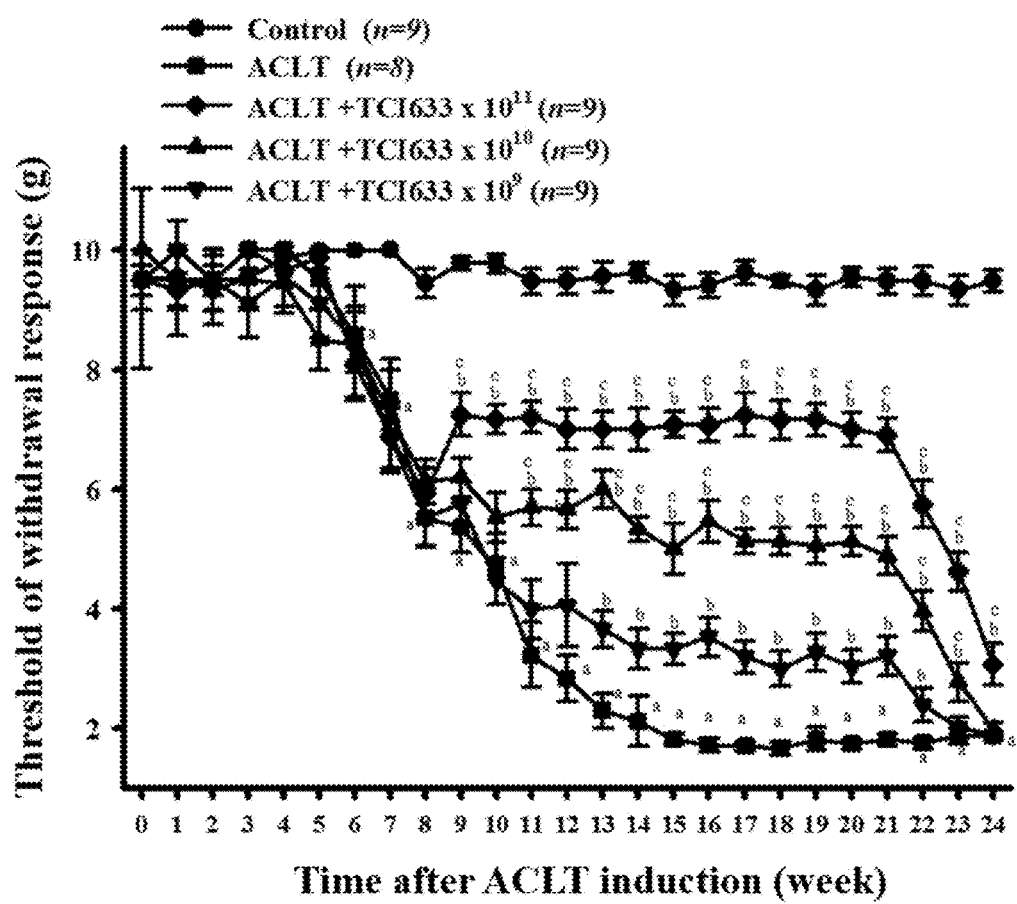
FIG. 4 is a comparative result diagram, showing the effects of different TCI633 doses on the ACLT-induced knee joint swelling as illustrated in the examples.

As shown in FIG. 4, ACLT group showed a significant increase in the difference in the widths of the left and right knee joints from weeks 1 to 24 compared with the control group. After the induction of arthritis, ACLT+TCI633 ($5 \times 10^{11}$ CFU) group showed a significant reduction in the difference in the widths of the left and right knee joints from weeks 9 to 24 compared with the ACLT group. The ACLT+TCI633 ($5 \times 10^{10}$ CFU) group showed a significant reduction in the difference in the widths of the left and right knee joints from weeks 8 to 11 and 14 to 22 compared with the ACLT group. The ACLT+TCI633 ($5 \times 10^{9}$ CFU) group showed a significant reduction in the difference in the widths of the left and right knee joints from weeks 13 to 22 compared with the ACLT group. Wherein, at weeks 8 to 22, the ACLT+TCI633 ($5 \times 10^{10}$ CFU) group and ACLT+TCI1633 ($5 \times 10^{11}$ CFU) group showed a significant reduction in the difference in the widths of the left and right knee joints compared with ACLT+TCI633 ($5 \times 10^{9}$ CFU) group. The above results indicate that TCI633 strain provided a significant effect on reducing ACLT-induced difference in the widths of the left and right knee joints, wherein the reduction was dose-dependent. As shown in Table 3, the percentage of inhibitory effect (%) on difference in the widths of the left and right knee joints in each of the ACLT+TCI633 groups tended to decrease after administration was stopped.

TABLE 3

| Groups | Week | | | | |
|---|---|---|---|---|---|
| | week 20 | week 21 | week 22 | week 23 | week 24 |
| ACLT | 100 ± 1.3 | 100 ± 1.04 | 100 ± 0.99 | 100 ± 1.12 | 100 ± 0.73 |
| ACLT + TCI633($5 \times 10^{9}$) | 88.29 ± 1.44 | 90.14 ± 1.16 | 95.83 ± 1.61 | 98.87 ± 0.85 | 98.85 ± 1.3 |
| ACLT + TCI633($5 \times 10^{10}$) | 81.13 ± 0.9 | 84.54 ± 1.17 | 93.59 ± 0.74 | 96.74 ± 1.02 | 96.92 ± 1.15 |
| ACLT + TCI633($5 \times 10^{11}$) Control group | 64.95 ± 1.07 | 67.38 ± 1.79 | 83.68 ± 2.05 | 90.41 ± 1.46 | 94.6 ± 1.23 |

EXAMPLE 5

Measurement of the Weight

Figure 5:
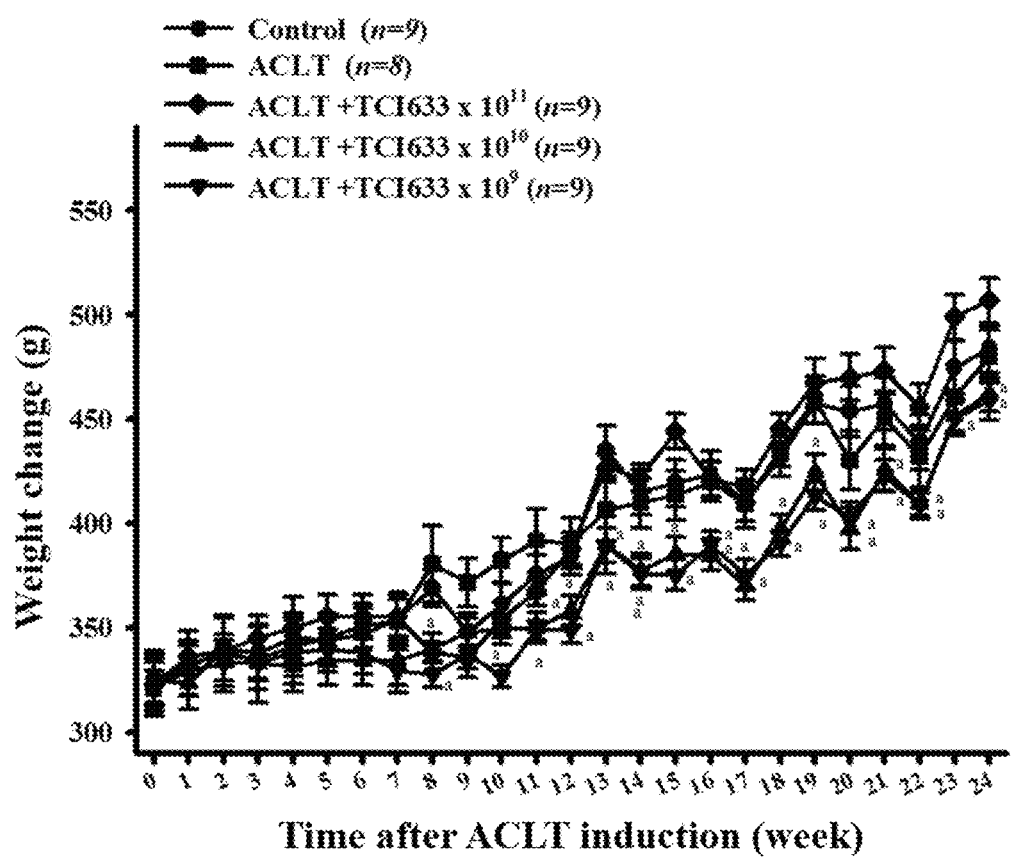
FIG. 5 is a comparative result diagram, showing the effects of different TCI633 doses on the weight change as illustrated in the examples.

Weight of rats were measured weekly before the ACLT (baseline) and from 1 to 24 weeks after the surgery, and the results are shown in FIG. 5.

As shown in FIG. 5, the ACLT group showed no significant difference in weight change from weeks 0 to 24 compared with the control group while showed weight gain over time. After the induction of arthritis, the ACLT+TCI633 ($5 \times 10^{11}$ CFU) group showed no significant difference in weight change from weeks 0 to 24 compared with the ACLT group while also showed weight gain over time. The ACLT+TCI633 ($5 \times 10^{10}$ CFU) group showed a significant reduction in weight gain at week 8 and from weeks 11 to 24 compared with the ACLT group. The ACLT+TCI633 ($5 \times 10^{9}$ CFU) showed a significant reduction in weight gain at week 8 and from weeks 10 to 24 compared with the ACLT group. The above results indicate that after ACLT surgery, TCI633 strain provided a significant slowing effect on the weight gain.

Example 6

Observation of the Pathological Sections (6-1) Collection, Fixation and Staining of Samples After completing the above animal behavior test, the rats were sacrificed and their knee tissue was removed. The knee tissue was fixed with 10% neutral formalin for 3 to 4 days, then soaked in a decalcifying fluid (100 g EDTA-2Na (ethylenediaminetetraacetic acid disodium salt dihydrate) in 1000 ml PBS) for 2 to 3 weeks to be decalcified. Then, the fixed, decalcified tissue was placed in the embedding cassette, and subjected to dehydration and waxing with 35% alcohol, 75% alcohol, 85% alcohol, 85% alcohol, 95% alcohol, 95% alcohol, 100% alcohol, 100% alcohol, 90% xyline/alcohol, 100% xyline, soft wax and hard wax sequentially. Thereafter, the tissue was embedded into a wax block by using a paraffin-embedding machine (CSA Embedding Center EC780-1; EC780-2). The wax block was cut into slices with a thickness of 1 μm using a paraffin slicer (Microm, HM340E, USA). Lastly, the tissue slices were subjected to hematoxylin-eosin staining and Safranin O/Fast green staining. The stained samples were observed under an optical microscope (DM 6000, Leica Inc., Germany) and the observation results were photographed by a microscope digital image output system (idea SPOT, Diagnostic instruments Inc. USA). The results are shown in FIG. 6, FIG. 7 and FIG. 8.

Figure 6:
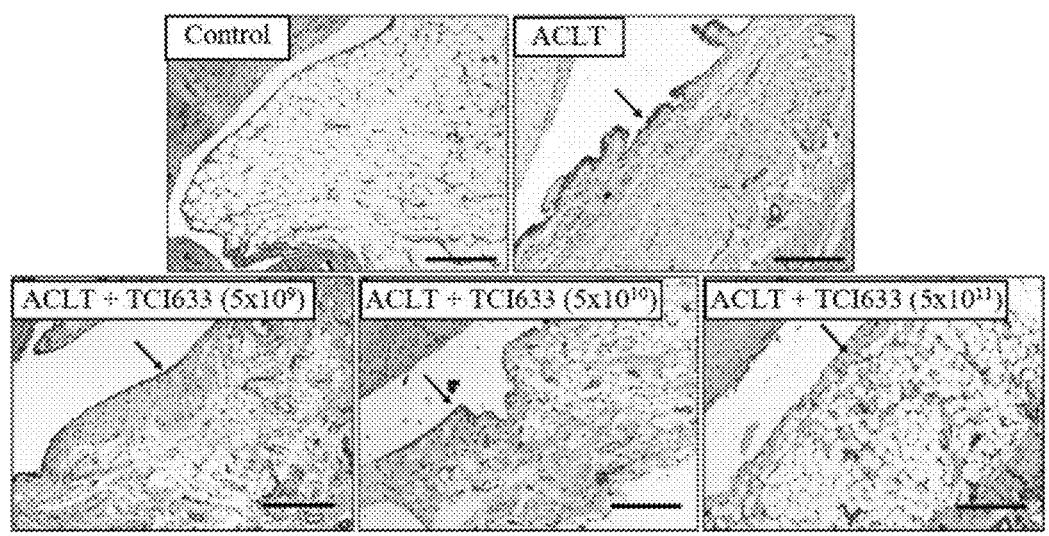
FIG. 6 is a group of tissue sections, showing the effects of different TCI633 doses on the inflammation in the synovial tissue of knee joints as illustrated in the examples.

(6-2) Effects of TCI633 Strain on the Inflammation of Synovial Tissue of Knee Joints As shown in FIG. 6, the ACLT group (i.e., rats that have been subjected to anterior cruciate ligament transection) showed significant levels of inflammatory blood cell infiltration, tissue hyperplasia and tissue hypertrophy in the synovial tissue compared with the control group. However, as compared to the ACLT group, the levels of inflammatory blood cell infiltration, tissue hyperplasia and tissue hypertrophy in the ACLT+TCI633 ($5 \times 10^{9}$ CFU) group, ACLT+TCI633 ($5 \times 10^{10}$ CFU) group and ACLT+TCI633 ($5 \times 10^{11}$ CFU) group all significantly reduced. The above results indicate that TCI633 strain can effectively reduce the ACLT-induced inflammation of synovial tissue.

(6-3) Effects of TCI633 Strain on Cartilaginous Tissue of Knee Joints

Figure 7:
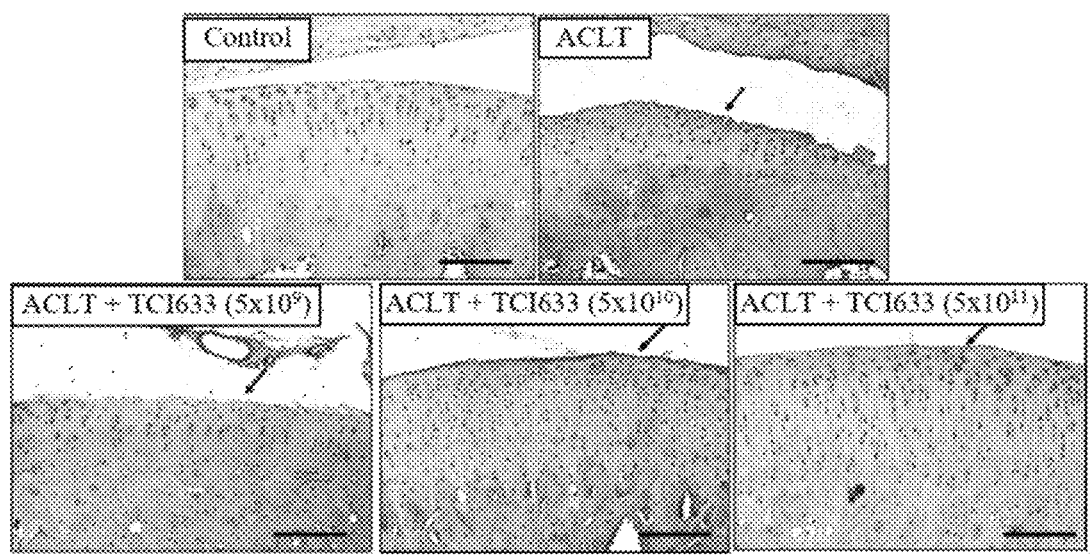
FIG. 7 is a group of tissue sections, showing the effects of different TCI633 doses on the bone tissue of knee joints as illustrated in the examples.
Figure 8:
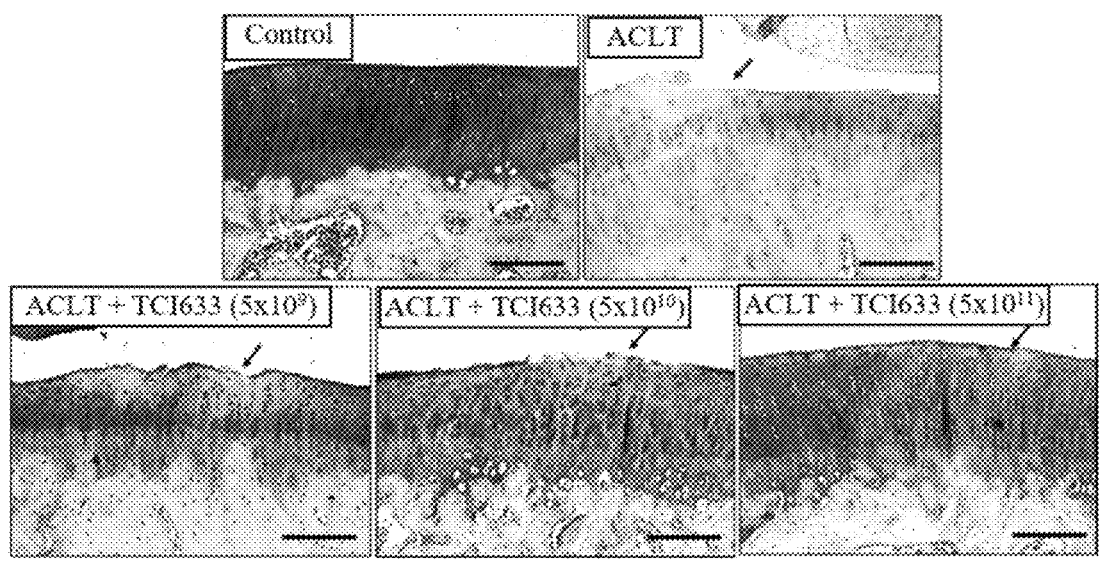
FIG. 8 is a group of tissue sections, showing the effects of different TCI633 doses on the cartilaginous tissue of knee joints as illustrated in the examples.

As shown in FIG. 7, the cartilaginous tissue surface of the ACLT group was significantly damaged (indicated by an irregular uneven appearance) compared with the control group. However, as compared to the ACLT group, the damage phenomenon of cartilaginous tissue surface in the ACLT+TCI633 ($5 \times 10^{10}$ CFU) group and ACLT+TCI633 ($5 \times 10^{11}$ CFU) group significantly reduced. The above results indicate that TCI633 strain can effectively protect cartilaginous tissue and relieve cartilage damage.

As shown in FIG. 8, as compared to the control group, the cartilaginous tissue surface of the ACLT group was significantly damaged, and the cartilage staining intensity in the ACLT group significantly decreased (i.e., the staining signal weakened, indicating that the content of cartilage matrix glycoprotein (proteoglycan) decreased, and proving that osteoarthritis was successfully induced in rats by ACLT). However, as compared to the ACLT group, the damage to cartilaginous tissue surface in the ACLT+TCI633 ($5\times10^9$ CFU) group, ACLT+TCI633 ($5\times10^{10}$ CFU) group and ACLT+TC633 ($5\times10^{11}$ CFU) group significantly reduced and the cartilage staining intensity significantly enhanced (i.e., the staining signal deepened).

The above results indicate that TCI633 strain can effectively protect cartilaginous tissue and relieve cartilage damage. On the other hand, as shown in FIG. 7 and FIG. 8, the number of chondrocytes in cartilaginous tissues of the ACLT+TCI633 ($5\times10^9$ CFU) group, ACLT+TCI633 ($5\times10^{10}$ CFU) group and ACLT+TCI633 ($5\times10^{11}$ CFU) group was significantly higher than that of the ACLT group.

Figure 9:
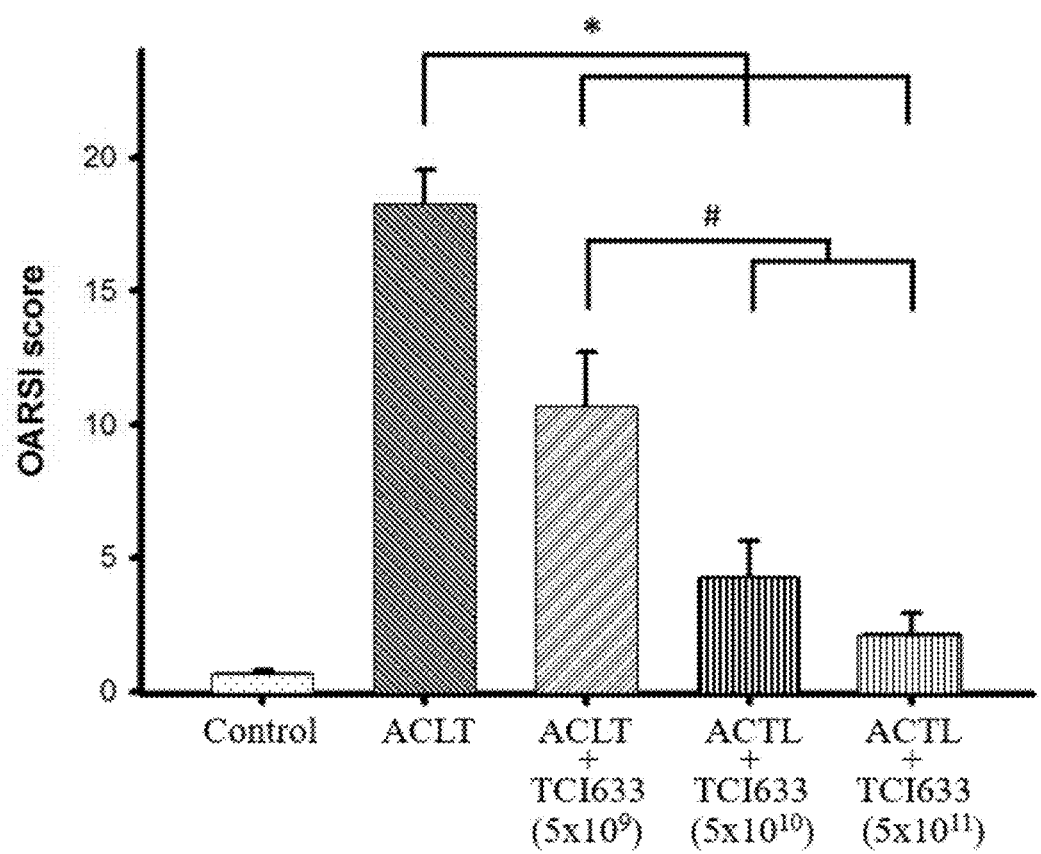
FIG. 9 is a comparative result diagram, showing the effects of different TCI633 doses on the cartilaginous tissue of knee joints as illustrated in the examples, wherein the effects were measured by the score system of Osteoarthritis Research Society International (OARSI score).

In addition, the effect of the TCI633 strain on the cartilaginous tissue of knee joints was also evaluated by the score system of Osteoarthritis Research Society International (OARSI score). While scoring, a semi-quantitative evaluation was conducted by using the OARSI grade (including six histological grades) and the stage of osteoarthritis recovery (including four histological stages). The total score was a result of multiplying the different grades and the different stages, and thus, ranged from 1 (normal articular cartilage) to 24 (no repair) (Pritzker et al., 2006). The results are shown in FIG. 9. As shown in FIG. 9, as compared to the control group, the score in the ACLT group increased significantly from weeks 24 after the anterior cruciate ligament was transected. However, as compared to the ACLT group, the score in the ACLT+TCI633 ($5\times10^9$ CFU) group, ACLT+TCI633 ($5\times10^{10}$ CFU) group and ACLT+TCI633 ($5\times10^{11}$ CFU) group reduced significantly, and the decline in the score was increased along with the increment in the administration dosage of the TCI633 strain. The results indicate that the TCI633 strain can effectively protect the cartilaginous tissue of the knee joints, and relieve the damage in the cartilaginous tissue of knee joints.

The above experimental results indicate that the TCI633 strain has significant therapeutic effects on arthritis, including relieving joint pain, alleviating joint swelling, relieving tissue inflammation, protecting cartilaginous tissue and increasing the number of chondrocytes in the cartilaginous tissues, while without causing side effects. Therefore, the TCI633 strain is safe for long term use for reducing the torment caused by pain, swelling and inflammation, as well as reducing the movement difficulties and inconveniences and improving the quality of the patient's life.

BRIEF DESCRIPTION OF REFERENCE NUMERALS

Not applicable.

DEPOSIT OF BIOLOGICAL MATERIAL

Depository institute: DSMZ (Deutsche Sammlung von Mikroorganismen and Zellkulturen GmbH)
Address: InhoffenstraBe 7 B, 38124 Braunschweig, GERMANY
Date: Dec. 2, 2013
Deposited biological material: *Streptococcus thermophilus* TCI633
Accession number: DSM 28121

What is claimed is:

1. A method of treating arthritis, comprising administering to a subject in need an effective amount of a dried bacterial powder of *Streptococcus thermophilus* TCI633 strain which was deposited at German Collection of Microorganisms and Cell Cultures (Deutsche Sammlung von Mikroorganismen und Zellkulturen GmbH, DSMZ) under accession number DSM 28121.

2. The method as claimed in claim 1, which is for at least one of relieving joint pain and alleviating joint swelling.

3. The method as claimed in claim 1, which is for relieving tissue inflammation.

4. The method as claimed in claim 1, which is for at least one of protecting cartilaginous tissues and increasing the number of chondrocytes in the cartilaginous tissues.

5. The method as claimed in claim 1, wherein the TCI633 strain is administered to the subject by oral administration.

6. The method as claimed in claim 1, wherein the TCI633 strain is administered to the subject by oral administration.

7. The method as claimed in claim 1, wherein the TCI633 strain is administered to the subject at a daily amount of at least $8.06\times10^8$ CFU/kg-body weight.

8. The method as claimed in claim 1, wherein the TCI633 strain is administered to the subject at a daily amount ranging from $8.06\times10^8$ CFU/kg-body weight to $8.06\times10^{10}$ CFU/kg-body weight.

9. The method as claimed in claim 2, wherein the TCI633 strain is administered to the subject by oral administration.

10. The method as claimed in claim 2, wherein the TCI633 strain is administered to the subject by oral administration.

11. The method as claimed in claim 2, wherein the TCI633 strain is administered to the subject at a daily amount of at least $8.06\times10^8$ CFU/kg-body weight.

12. The method as claimed in claim 2, wherein the TCI633 strain is administered to the subject at a daily amount ranging from $8.06\times10^8$ CFU/kg-body weight to $8.06\times10^{10}$ CFU/kg-body weight.

13. The method as claimed in claim 3, wherein the TCI633 strain is administered to the subject by oral administration.

14. The method as claimed in claim 3, wherein the TCI633 strain is administered to the subject by oral administration.

15. The method as claimed in claim 3, wherein the TCI633 strain is administered to the subject at a daily amount of at least $8.06\times10^8$ CFU/kg-body weight.

16. The method as claimed in claim 3, wherein the TCI633 strain is administered to the subject at a daily amount ranging from $8.06\times10^8$ CFU/kg-body weight to $8.06\times10^{10}$ CFU/kg-body weight.

17. The method as claimed in claim 4, wherein the TCI633 strain is administered to the subject by oral administration.

18. The method as claimed in claim 4, wherein the TCI633 strain is administered to the subject by oral administration.

19. The method as claimed in claim 4, wherein the TCI633 strain is administered to the subject at a daily amount of at least $8.06\times10^8$ CFU/kg-body weight.

20. The method as claimed in claim 4, wherein the TCI633 strain is administered to the subject at a daily amount ranging from $8.06\times10^8$ CFU/kg-body weight to $8.06\times10^{10}$ CFU/kg-body weight.

* * * * *